United States Patent [19]

Tanba et al.

[11] Patent Number: 4,734,492
[45] Date of Patent: Mar. 29, 1988

[54] MACROLIDE ANTIBIOTIC M 119

[75] Inventors: Hiroyuki Tanba; Kazuyoshi Adachi; Tomiko Kawasaki, all of Maebashi, Japan

[73] Assignee: Kirin Beer Kabushiki Kaisha, Tokyo, Japan

[21] Appl. No.: 884,403

[22] Filed: Jul. 11, 1986

[30] Foreign Application Priority Data

Jul. 16, 1985 [JP] Japan ................................ 60-156396

[51] Int. Cl.$^4$ ............................................ C07H 17/08
[52] U.S. Cl. ...................................... 536/7.1; 435/75
[58] Field of Search ......................................... 536/7.1

[56] References Cited

U.S. PATENT DOCUMENTS 3,853,842 12/1974 Kishi et al. ............................ 536/7.1
4,358,584 11/1982 Nash et al. ............................ 536/7.1

Primary Examiner—J. R. Brown
Assistant Examiner—Elli Preselev
Attorney, Agent, or Firm—Ladas & Parry

[57] ABSTRACT

Disclosed is a novel macrolide antibiotic, M 119, of the formula (A):

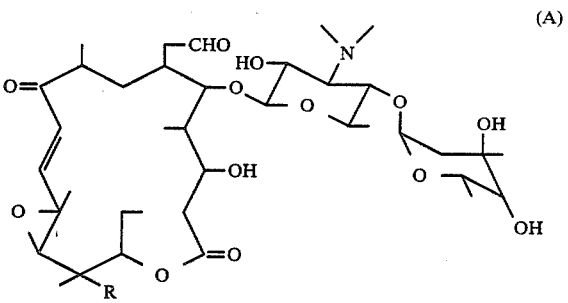

wherein the substituent R designates either (a) or (d):
(a) R: H
(d) R: OH.

The antibiotic M 119 has antimicrobial activity, particularly against Gram-positive bacteria, typical pathogenic bacteria falling under Gram-negative bacteria such as *Haemophilus influenzae,* and mycoplasmas, and is effective against infections induced by such bacteria.

1 Claim, 8 Drawing Figures

δ ( ppm )

F I G. I

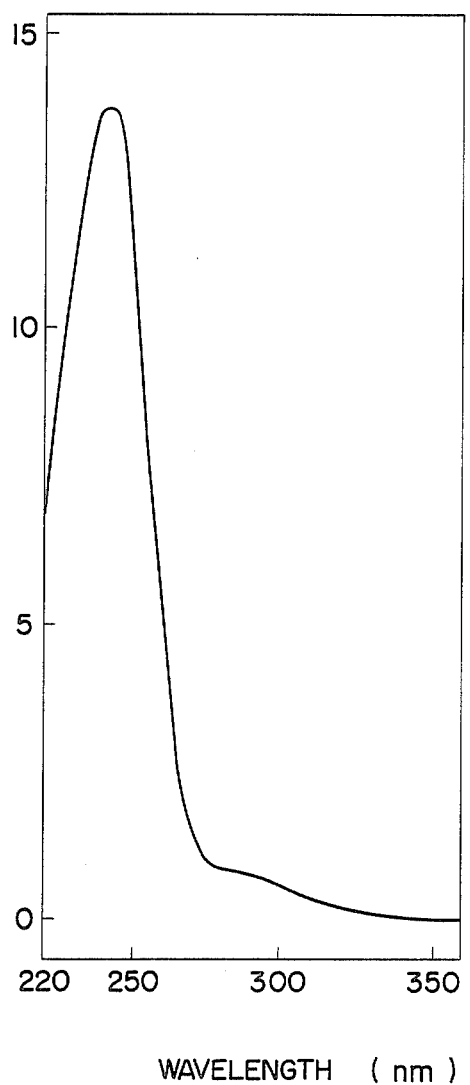
F I G. 5

MACROLIDE ANTIBIOTIC M 119

BACKGROUND OF THE INVENTION

The present invention relates to a novel macrolide antibiotic, M 119.

Macrolide compounds assume an important position in medicine (as antimicrobial agents), and various macrolide compounds have been proposed so far.

Generally, the physiological activities of chemical substances depend greatly on their chemical structures. There has been a constant demand, therefore, for macrolide compounds which differ from conventional ones in terms of the aglycone moiety and saccharide moiety or substituents.

SUMMARY OF THE INVENTION

The present invention contributes toward meeting the above-mentioned demand. More particularly, this invention provides a novel macrolide antibiotic, M 119, of the formula (A):

(A)

wherein the substituent R designates either (a) or (d):
(a) R:H
(d) R:OH.

Depending on the type of the substituent R, the substance M 119 includes two species, viz. M 119-a and M 119-d.

BRIEF DESCRIPTION OF THE DRAWINGS

In the drawings:

FIG. 5 is a graph showing the ultraviolet absorption spectrum of M 119-d;

DETAILED DESCRIPTION OF THE INVENTION

Novel macrolide antibiotic M 119

I. Physicochemical properties

The physicochemical properties of the substance M 119 are set forth below.

A. M 119-a (R in the formula (A) is (a))
(1) Color and form: Colorless powder.
(2) Molecular formula: $C_{38}H_{63}NO_{13}$.
(3) Elementary analysis:

|  | C | H | N |
|---|---|---|---|
| Found (%) | 61.50 | 8.91 | 1.72 |
| Calcd. (%) | 61.54 | 8.50 | 1.89 |

Figure 1:
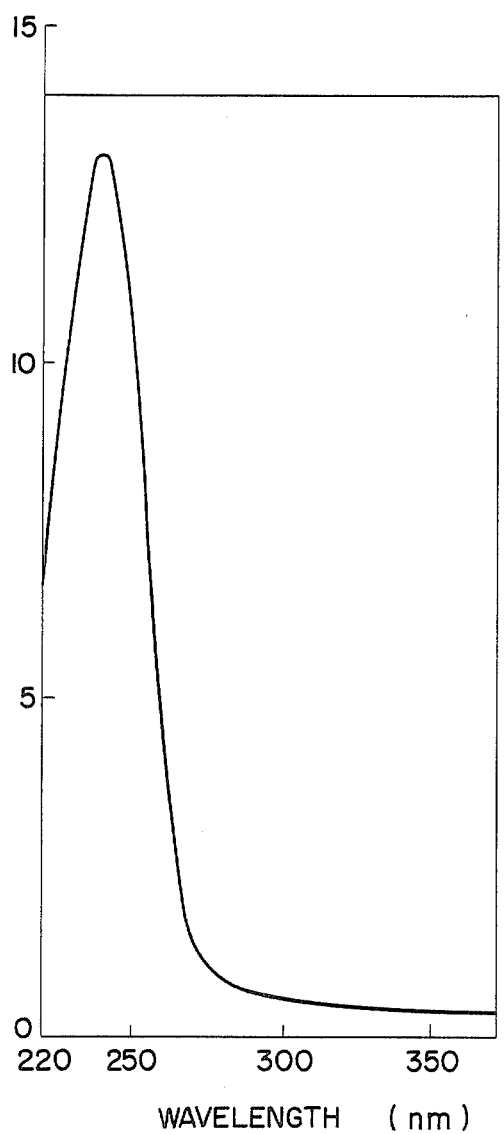
FIG. 1 is a graph showing the ultraviolet absorption spectrum of M 119-a.

(4) Molecular weight: 741 (by mass spectrum).
(5) Melting point: 174.5°~176° C.
(6) specific rotatory power: $[\alpha]^{24}$ −63° (C: 0.5, in methanol).
(7) Ultraviolet absorption spectrum: FIG. 1.

$\lambda_{max}^{MeOH} nm(\epsilon):240(13,000)$.

Figure 2:
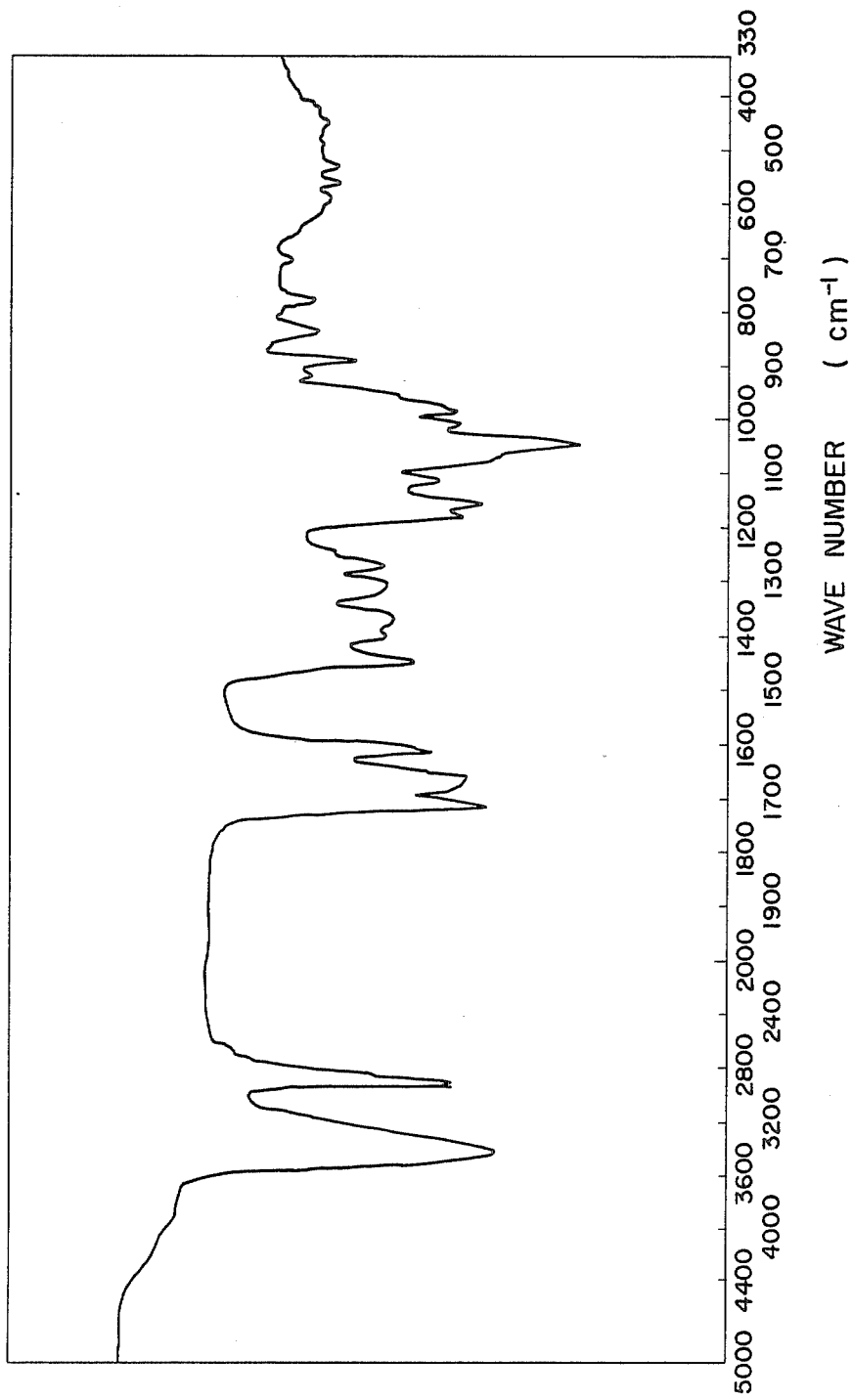
FIG. 2 is a graph showing the infrared absorption spectrum of M 119-a.

(8) Infrared absorption spectrum: FIG. 2 (KBr method): 3450, 2970, 2930, 2880, 1720, 1670, 1620, 1450, 1405, 1380, 1310, 1275, 1180, 1160, 1115, 1050, 1015, 990 cm$^{-1}$.

Figure 3:
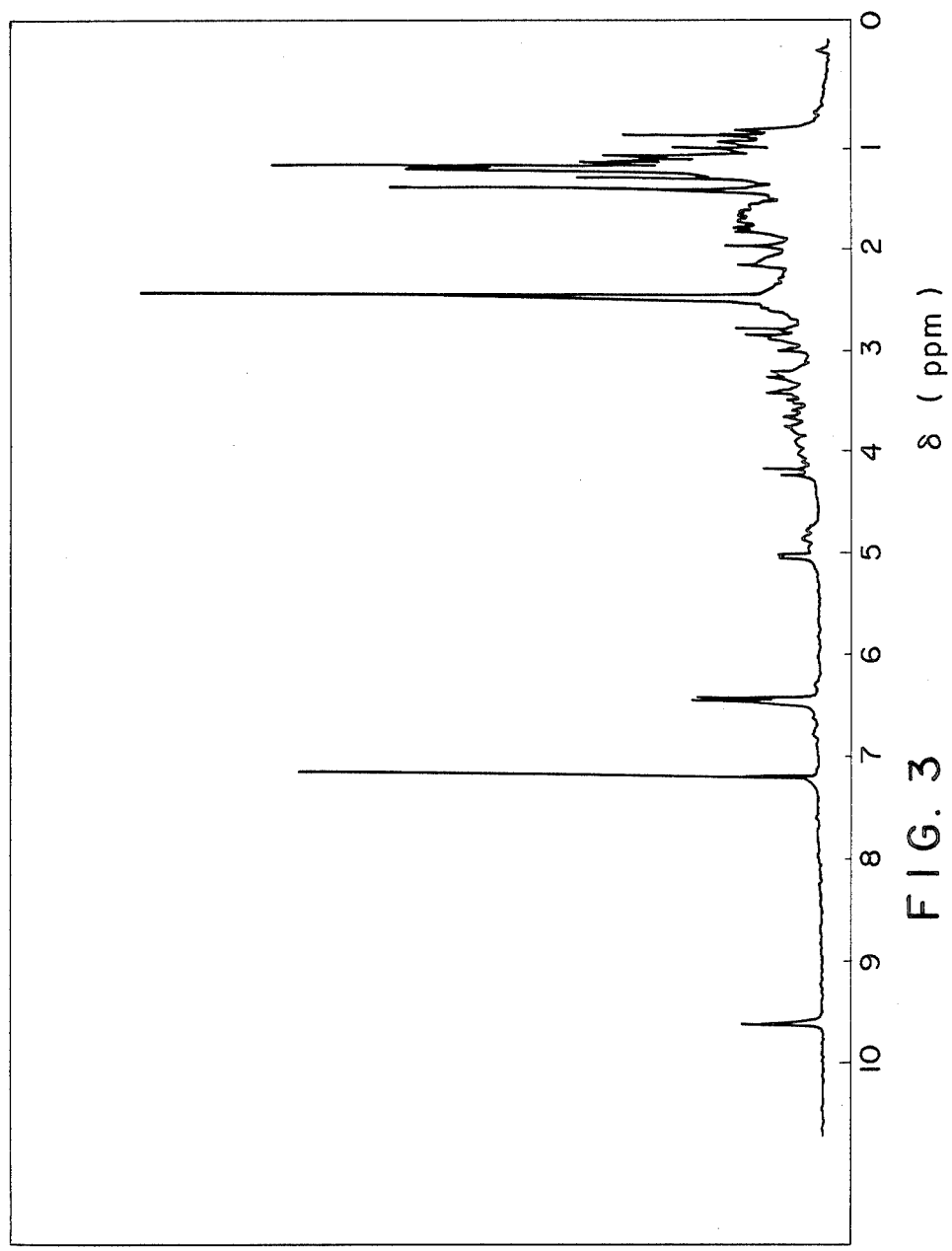
FIG. 3 is a graph showing the $^1$H-NMR spectrum of M 119-a.
Figure 4:
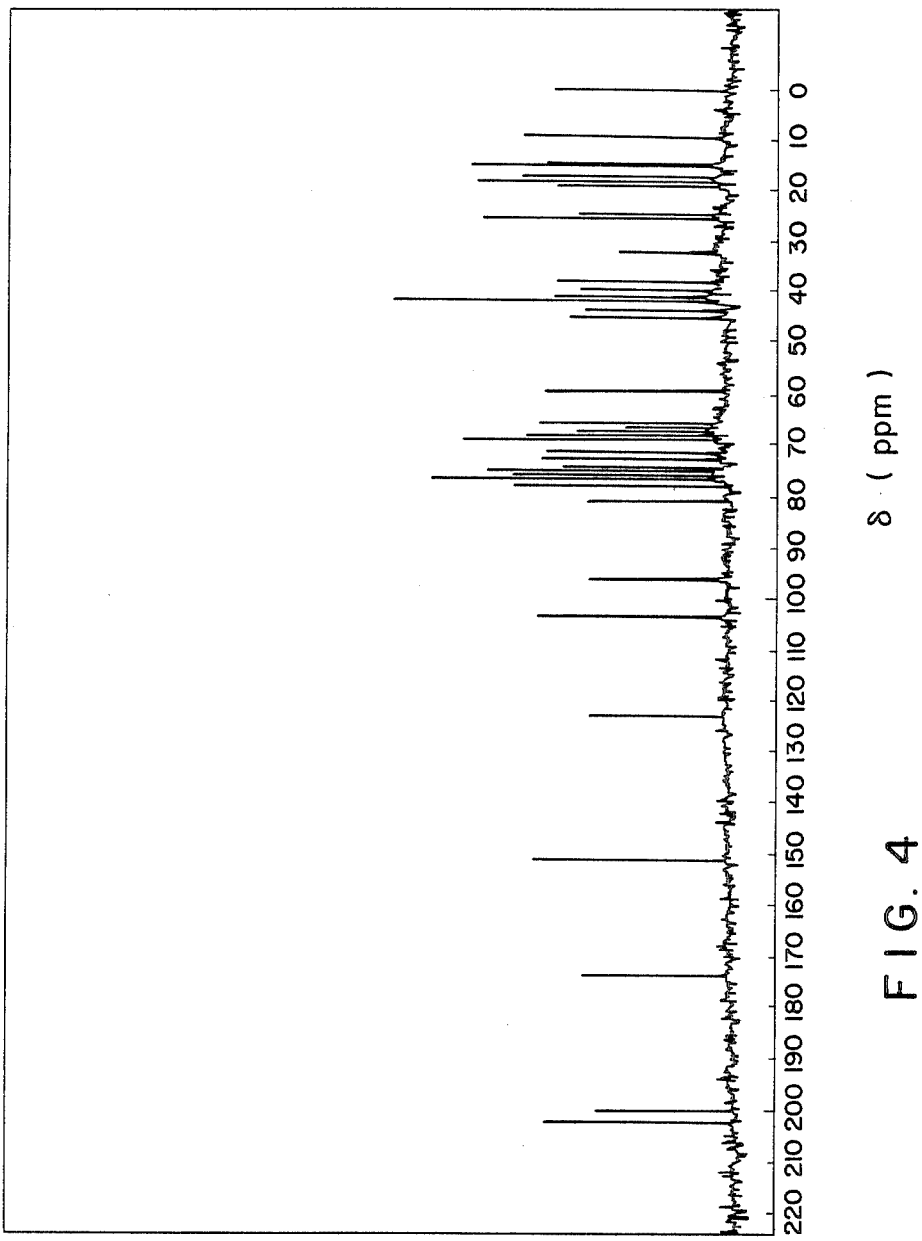
FIG. 4 is a graph showing the $^{13}$C-NMR spectrum of M 119-a.

(9) NMR spectrum: $^1$H-FIG. 3 (TMS Standard, in CDCl$_3$, 100 MHz); $^{13}$C-FIG. 4 (TMS Standard, in CDCl$_3$, 25 MHz).

(10) Silica gel (Merck & Co., Inc.) thin layer chromatography: Chloroform: methanol (9:1) $R_f=0.52$.

(11) Color reaction: Dark blue by thin layer chromatography with a vanillin reagent.

(12) Solubility: Soluble in methanol and chloroform but insoluble in hexane, ether and water.

B. M 119-d (R in the formula (A) is (d))
(1) Color and form: Colorless powder.
(2) Molecular formula: $C_{38}H_{63}NO_{14}$.
(3) Elementary analysis:

|  | C | H | N |
|---|---|---|---|
| Found (%) | 60.19 | 8.47 | 1.76 |
| Calcd. (%) | 60.24 | 8.32 | 1.85 |

(4) Molecular weight: 757 (by mass spectrum).
(5) Melting point: 144~146° C.
(6) Specific rotatory power: $[\alpha]^{24}$ −72° (C: 0.5, in methanol).
(7) Ultraviolet absorption spectrum: FIG. 5.

$\lambda_{max}^{MeOH} nm(\epsilon)=240(13,700)$.

Figure 6:
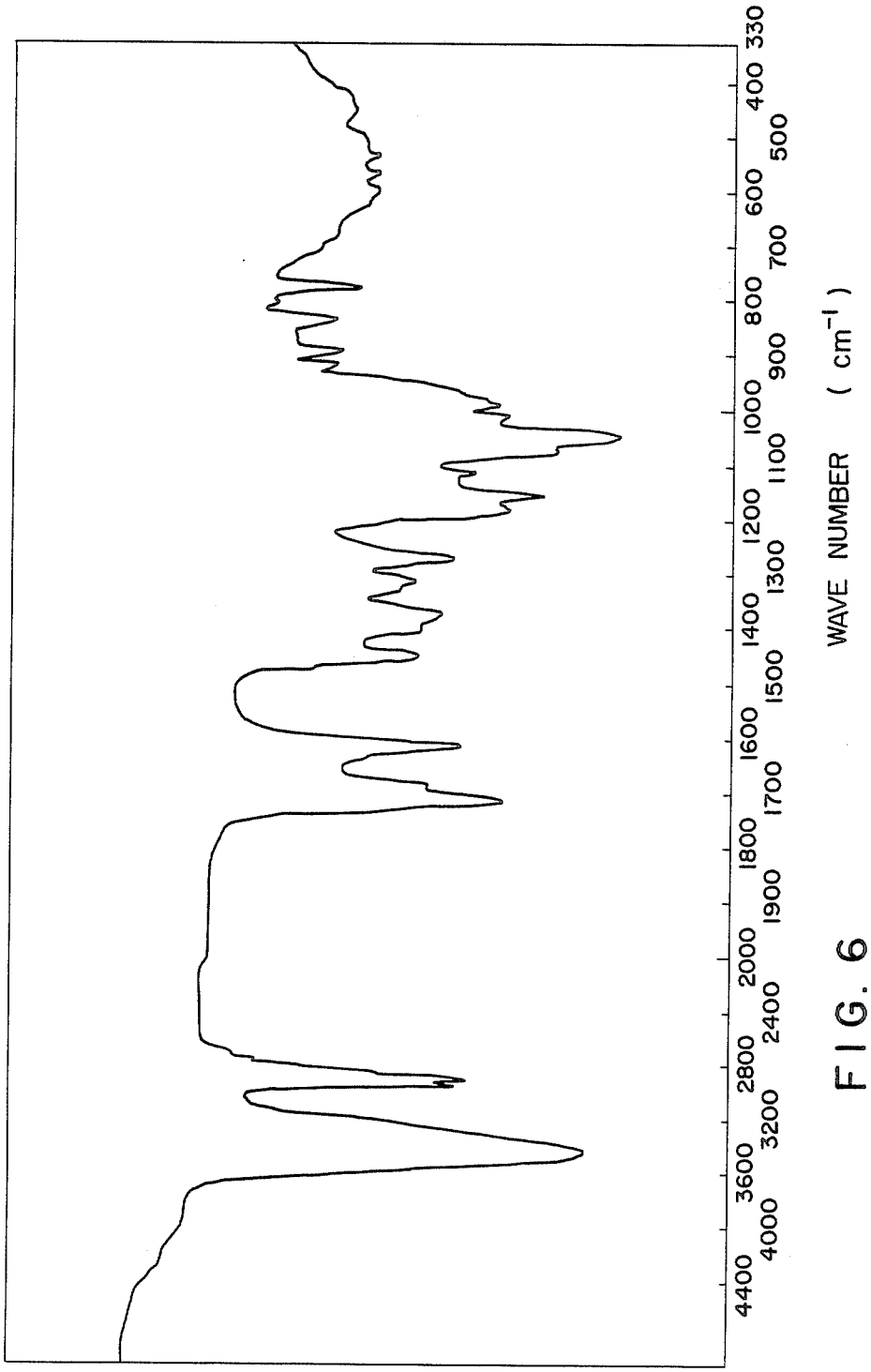
FIG. 6 is a graph showing the infrared absorption spectrum of M 119-d.

(8) Infrared absorption spectrum: FIG. 6 (KBr method) 3430, 2970, 2930, 2880, 1720, 1685, 1620, 1450, 1405, 1375, 1330, 1315, 1280, 1180, 1160, 1115, 1080, 1050, 1015, 990 cm$^{-1}$.

Figure 7:
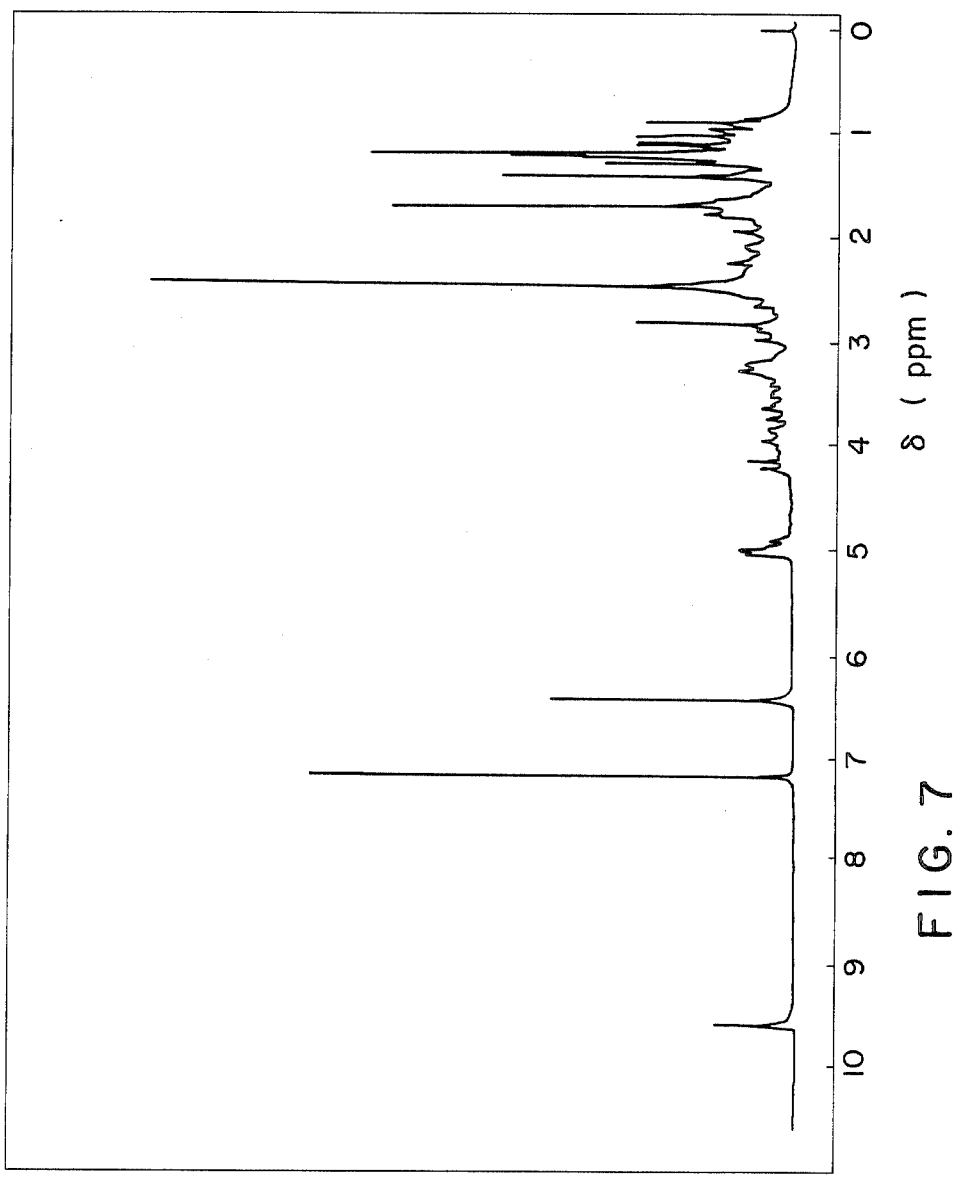
FIG. 7 is a graph showing the $^1$H-NMR spectrum of M 119-d.
Figure 8:
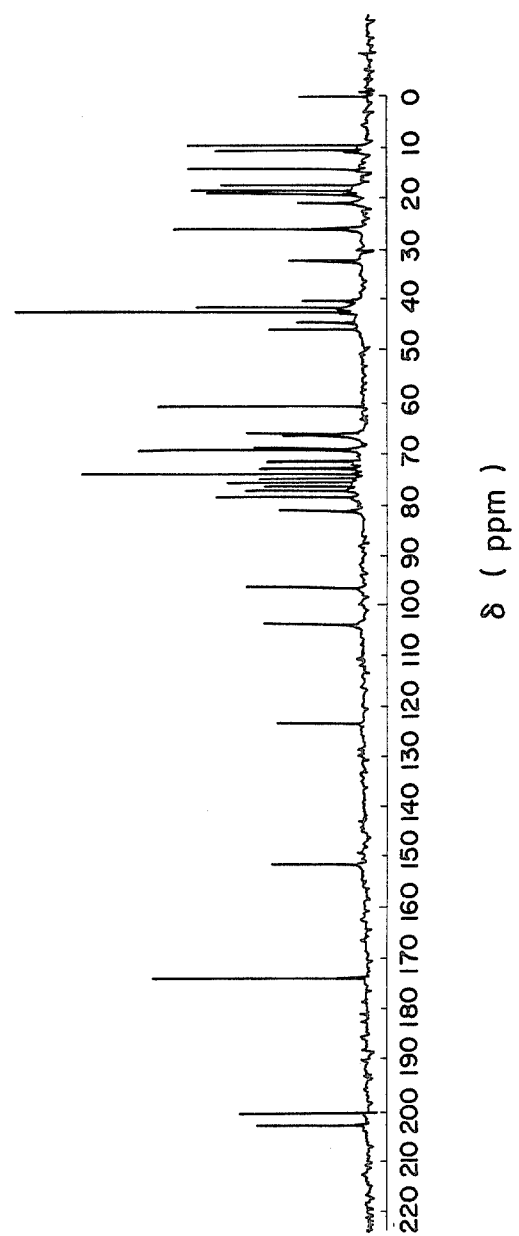
FIG. 8 is a graph showing the $^{13}$C-NMR spectrum of M 119-d.

(9) NMR spectrum: $^1$H-FIG. 7 (TMS Standard, in CDCl$_3$, 100 MHz); $^{13}$C-FIG. 8 (TMS Standard, in CDCl$_3$, 25 MHz).

(10) Silica gel (Merck & Co., Inc.) thin layer chromatography: Chloroform: methanol (9:1) $R_f=0.46$.

(11) Color reaction: Dark blue by thin layer chromatography with a vanillin reagent.

(12) Solubility: Soluble in methanol and chloroform but insoluble in hexane, ether and water.

II. Chemical structure

In view of the above physicochemical properties including NMR spectrum, the substance M 119 has been found to have a chemical structure as shown by the formula (A) illustrated earlier.

Production of the substance M 119

I. Outline

The novel macrolide antibiotic M 119 has been heretofore obtained only by the cultivation of microorganisms. It may be possible, however, to produce this antibiotic by synthetic chemical or microbiological modification of related compounds or to produce it by total chemical synthesis.

The cultivation technique uses strains capable of producing M 119. More specifically, we have found that an alkalophilic actinomycete, strain M 119, isolated by us produces M 119. Other suitable strains which produce M 119 can be isolated from the natural environment by any methods conventionally employed for the isolation of antibiotics-producing microorganisms. It may also be possible to increase the M 119 output by subjecting M 119-producing microorganisms including the alkalophilic actinomycete, strain M 119, to irradiation with radioactive rays or to some other treatments. It is also possible to induce M 119-producing microorganisms by gene manipulation procedure, for example, by incorporating the gene DNA of the strain M 119 which bears genetic information as to the production of M 119 into other microorganisms by way of transformation or cell fusion. It is to be understood that these microorganisms induced from the above strain are also included within the scope of the present invention.

II. Strain M 119

Strain M 119, a macrolide antibiotic M 119-producing actinomyces discovered by us, will be described in detail below.

1. Origin and Accession No.

Strain M 119 is an actinomycete isolated from the soil collected from a truck farm in Okinawa-shi, Okinawaken, Japan. This strain was deposited on July 16, 1985 with the Fermentation Research Institute, Agency of Industrial Science and Technology, Ministry of International Trade and Industry of Japan, 1-3, Higashi 1 chome, Yatabe-machi, Tsukuba-gun, Ibaraki-ken 305, Japan, where it was assigned the accession number FERM-P No. 8351. This strain now bears the accession number FERM BP-1075 under the terms of the Budapest Treaty on the International Recognition of the Deposit of Microorganisms for the Purposes of Patent Procedure. This depository fully complies with the rules of the Budapest Treaty. Specifically, it fully complies with Rule 11.3 of the Budapest Treaty whereby the organism is available to the public on patent grant and with Rule 9 of the same Treaty which requires the maintenance of the organism for a period of at least 30 years after the date of deposit.

2. Microbiological characteristics of strain M 119

Strain M 119 has the following microbiological characteristics.

This strain is alkalophilic, scarcely growing at a pH of about 6.0 to 7.0, at which ordinary actinomycetes grow, and growing best at a pH of 10.0 to 10.5. Thus, all of the culture media used in the tests on the microbiological characteristics of strain M 119 set forth hereinbelow were adjusted to a pH of 10.0 to 10.5.

(1) Morphology

Strain M 119 grows well in agar, and the well branched substrate mycelium thereof extends aerial hyphae which are branched monopodially and form straight to slightly curved (Rectus~Flexibilis) spore chains consisting of 20 or less spores. The spores are of an elliptical or cylindrical shape (0.4 to $0.6\mu \times 0.6$ to $0.8\mu$) and have a smooth surface. No flagellar spores, sporangia or fragmented substrate mycelia are observed.

(2) Cultural characteristics

The cultural characteristics of strain M 119 cultivated on various culture media are as summarized in Table 1. (Observations were made after cultivation at 27° C. for 3 weeks, unless otherwise noted.)

(3) Physiological properties

The physiological properties of strain M 119 are as set forth in Table 2.

(4) Carbon utilization (on Pridham-Gottlieb agar medium)

Utilization of various carbon sources is as shown in Table 3.

(5) Cell wall composition

The diaminopimelic acid contained in the cell hydrolyzate is of the meso type.

TABLE 1

| | Cultural Characteristics | | | |
|---|---|---|---|---|
| Medium | Growth | Aerial mycelium | Reverse side pigment | Soluble pigment |
| Sucrose-nitrate agar | Moderate Light olive gray | Moderate Powdery Yellowish white | Yellowish white | None |
| Glucose-asparagine agar | Poor Light olive gray | None | Yellowish white | None |
| Glycerol-asparagine agar | Moderate Yellowish white | Moderate Powdery Yellowish white | Yellowish white | None |
| Inorganic salts-starch agar | Very poor Yellowish white | None | Light olive gray | None |
| Tyrosine agar | Moderate Yellowish white | Moderate Powdery Yellowish white | White to Yellowish white | None |
| Nutrient agar | Moderate Pale yellowish brown | Poor, Powdery White to yellowish white | Pale yellowish brown | None |
| Yeast extract-malt extract agar | Good Pale yellowish brown | Moderate Powdery Yellowish white | Pale yellow to Pale yellowish brown | None |
| Oatmeal agar | Moderate Pale yellowish | Very poor Powdery | Yellowish white | None |

TABLE 1-continued

| Medium | Growth | Cultural Characteristics | | Soluble pigment |
|---|---|---|---|---|
| | | Aerial mycelium | Reverse side pigment | |
| | brown | White | | |

TABLE 2

| Physiological Properties | |
|---|---|
| Growth temperature range | 20–42° C. |
| Suitable pH range for growth | 7.0–11.0 |
| Halotolerance (NaCl) | <10.0% |
| Production of melanoid pigment | |
| Tyrosine agar | − |
| Peptone-yeast extract-iron agar | − |
| Tryptone-yeast extract broth | − |
| Hydrolysis of starch | − |
| Liquefaction of gelatin | + |
| Coagulation of skim milk | − |
| Peptonization of skim milk | + |
| Nitrate reduction | + (weak) |
| Productin of hydrogen sulfide | + |
| Decomposition of cellulose | − |

Note:
+ = positive
− = negative

TABLE 3

| Carbon Utilization | |
|---|---|
| D-Glucose | ± |
| L-Arabinose | − |
| D-Xylose | ± |
| i-Inositol | − |
| D-Mannitol | + |
| D-Fructose | ± |
| Rhamnose | − |
| Sucrose | + |
| Raffinose | − |

Note:
+ = positive utilization
± = questionable utilization
− = no utilization

In view of the above data, strain M 119 is classified under actinomycetes. More particularly, this strain grows best in the alkaline pH range and thus falls under alkalophilic actinomycetes.

III. Cultivation for production of M 119

The macrolide antibiotic, M 119, can be prepared by cultivating an M 119-producing actinomycete aerobically in a suitable medium and recovering the objective product from the culture.

For the culture media, it is possible to use those containing any nutrient sources which can be utilized by the M 119-producing strains. For example, glucose, sucrose, maltose, starch, molasses, oils and fats can be used as carbon sources. Examples of nitrogen sources are organic materials such as soybean meal, wheat germ, meat extract, peptone, dry yeast, yeast extract and cornsteep liquor, and inorganic materials such as ammonium salts or nitrates. If necessary, inorganic salts such as sodium chloride, potassium chloride, phosphates and salts of heavy metals can also be added. In order to prevent foaming during fermentation, suitable antifoaming agents may be added by a conventional method.

The most suitable method of cultivation is submerged aerobic liquid cultivation which is employed widely for the production of antibiotics. A suitable cultivation temperature is 20° to 37° C., preferably 25° to 32° C. The production output of the substance M 119 reaches a maximum after 3 to 7 days of shake culture, and after 2 to 6 days of cultivation under aeration and stirring.

A culture in which M 119 is accumulated can thus be obtained. The M 119 can be harvested from the culture by any suitable method. One such method is based on extraction. For example, the M 119 in the filtrate of the culture can be harvested by extraction with a water-immiscible solvent such as ethyl acetate, butyl acetate, chloroform, or butanol. (A high extraction efficiency is achieved when the culture filtrate is neutral or weakly basic.) It is also possible to subject the culture as such to the above-mentioned extraction procedure without preliminarily isolating cells.

Another method for harvesting the M 119 from the culture is based on adsorption. An M 119-containing liquid material, such as a culture filtrate or an extract obtained by the extraction procedure described hereinbefore, is subjected, for example, to column chromatography using a suitable adsorbent, such as activated carbon, alumina, silica gel or "DIAION HP 20" (supplied by Mitsubishi Kasei K.K., Japan). The desired M 119 adsorbed onto the adsorbent is then eluted therefrom. The resulting M 119 solution is concentrated to dryness under reduced pressure to obtain a crude M 119 product.

The crude M 119 product thus obtained can be purified by carrying out the aforementioned extraction or adsorption procedure, if necessary, in combination, over a necessary number of times. For example, purification can be accomplished by an appropriate combination of column chromatography using an adsorbent, such as silica gel or alumina, or a gel filter; liquid chromatography using a suitable solvent; and countercurrent distribution. A specific example of the purification method comprises dissolving the crude M 119 product in a small quantity of chloroform, applying the solution to a silica gel column, and developing the column with a suitable solvent to elute the active components of the substance M 119. As a result, M 119-a and M 119-d are respectively isolated as single substances, which are concentrated and crystallized from a suitable solvent to obtain M 119-a or M 119-d as a colorless powder.

Physiological activities of the substance M 119

The substance M 119 exhibits antimicrobial activity against various microorganisms, and the minimum inhibitory concentration (MIC) of this substance determined by the agar dilution method was as shown in Table 4 below. Also shown in the same table are the MIC's obtained for josamycin (JM) and erythromycin (EM) as controls.

TABLE 4-a

| Microorganism | MIC's of M 119-a and M 119-d (μg/ml) | | | |
|---|---|---|---|---|
| | M 119-a | M 119-d | JM | EM |
| *Staphylococcus aureus* FDA 209PJC-1 (MS-1) | 0.20 | 0.78 | 0.20 | 0.20 |

TABLE 4-a-continued

| Microorganism | MIC's of M 119-a and M 119-d (μg/ml) | | | |
|---|---|---|---|---|
| | M 119-a | M 119-d | JM | EM |
| *Staphylococcus aureus* Terajima (MS-1) | 0.78 | 3.13 | 0.78 | 0.20 |
| *Staphylococcus aureus* MS 353 (MS-1) | 0.78 | 3.13 | 0.78 | 0.20 |
| *Streptococcus pyogenes* Cook (MS-1) | 0.20 | 0.78 | 0.20 | 0.20 |
| *Bacillus subtilis* ATCC 6633 (MS-1) | 0.20 | 0.78 | 0.39 | <0.10 |
| *Bacillus cereus* IAM 1729 | 0.39 | 1.56 | 0.39 | 0.20 |
| *Micrococcus luteus* ATCC 9341 (MS-1) | <0.10 | 0.20 | <0.10 | <0.10 |
| *Staphylococcus aureus* MS 15009 (pI258) Mac[r] | >100 | >100 | >100 | >100 |
| *Staphylococcus aureus* MS 12917 Mac[r] | >100 | >100 | >100 | >100 |
| *Escherichia coli* NIHJ-JC-2 (MS-1) | >100 | >100 | >100 | 100 |
| *Escherichia coli* K12 C600 (MS-1) | 100 | 100 | >100 | 50 |
| *Klebsiella pneumoniae* PCI-602 (MS-1) | 12.5 | 12.5 | 12.5 | 6.25 |
| *Salmonella typhimurium* IID971 (MS-1) | >100 | >100 | >100 | 100 |
| *Salmonella typhi* 901 (MS-1) | 100 | 100 | >100 | 50 |
| *Salmonella paratyphi* 1015 (MS-1) | 50 | 25 | 100 | 25 |
| *Salmonella schottmuelleri* 8006 (MS-1) | 100 | 25 | >100 | 50 |
| *Salmonella enteritidis* G 14 (MS-1) | >100 | >100 | >100 | 100 |
| *Serratia marcescens* IAM 1184 (MS-1) | >100 | >100 | >100 | 100 |
| *Pseudomonas aeruginosa* IFO 3445 (MS-1) | >100 | >100 | >100 | >100 |
| *Pseudomonas aeruginosa* NCTC 10490 (MS-1) | >100 | >100 | >100 | >100 |
| *Pseudomonas aeruginosa* PAO 1 (MS-1) | >100 | >100 | >100 | >100 |
| *Proteus morganii* IFO 3848 (MS-1) | 50 | 50 | >100 | 25 |
| *Proteus vulgaris* OX-19 (MS-1) | >100 | >100 | >100 | >100 |
| *Proteus rettgeri* IFO 3850 (MS-1) | >100 | >100 | >100 | >100 |
| *Enterobacter aerogenes* ATCC 13048 (MS-1) | >100 | 100 | >100 | 100 |
| *Enterobacter cloacae* 963 (MS-1) | >100 | >100 | >100 | >100 |
| *Haemophilus influenzae* (clinically isolated five strains) | 1.56~6.25 | — | 3.13~6.25 | 1.56~3.13 |
| *Mycoplasma pneumoniae* | 0.10 | | 0.20 | 0.10 |

Note: "Mac[r]" stands for a constitutive macrolide resistant bacterium.

As is apparent from Table 4, the substance M 119 according to the present invention has antimicrobial activity, particularly against Gram-positive bacteria, typical pathogenic bacteria falling under Gram-negative bacteria such as *Haemophilus influenzae*, and *mycoplasmas*, and thus can be used as an antibiotic effective against infections induced by such bacteria.

EXPERIMENTAL EXAMPLES

In the following examples, "%" is "w/v%".

Example 1

100 ml of a pre-culture medium containing 3% of glycerol, 1% of cornsteep liquor, 0.3% of dry yeast, 0.35% of CaCO$_3$ and 1% of Na$_2$CO$_3$ (pH 10.6) was charged into a 500-ml Erlenmeyer flask and inoculated with a platinum loopful of an alkalophilic actinomycete, strain M 119. The inoculated medium was subjected to shake culture for 3 days at 27° C. to prepare an inoculum.

150 liters of a medium having the same composition as the pre-culture medium was charged into a 300-liter fermenter, and 3 liters of the inoculum was added thereto. The fermentation was carried out for 3 days at 27° C. at 0.5 v.v.m. and 150 r.p.m.

After the fermentation was completed, CELITE was added to the fermented mash, which was then filtered under pressure. To 150 liters of the culture filtrate including wash liquor was added an equal volume of butyl acetate, and the resultant filtrate was subjected to extraction. The butyl acetate layer was concentrated under reduced pressure to obtain 14 g of a crude M 119-a and M 119-d product.

Example 2

The crude M 119-a and M 119-d product was dissolved in chloroform, washed with water, dehydrated with anhydrous sodium sulfate, and then concentrated. The concentrate was supplied to a silica gel column (3 cm Φ×25 cm) equilibrated with chloroform and developed with a chloroform-methanol mixture, whereby an M 119-a fraction was eluted with a 50:1 chloroform-methanol mixture while an M 119-d fraction was eluted with a 20:1 chloroform-methanol mixture.

The M 119-a fraction was concentrated and subjected again to silica gel chromatography (3 cm Φ×25 cm) using a 55:30:4 hexane-ethyl acetate-methanol solvent mixture. The M 119-a fraction thus purified was concentrated to dryness to obtain 100 mg of M 119-a.

The M 119-d fraction, on the other hand, was concentrated and then subjected to gel filtration (2.5 cm Φ×31 cm) with TOYOPEARL HW 40 (supplied by Toyo Soda Mfg. Co., Ltd., Japan). The purified M 119-d fraction was concentrated to dryness to obtain 420 mg of M 119-d.

What is claimed is:

1. A macrolide antibiotic, M 119, of the formula:

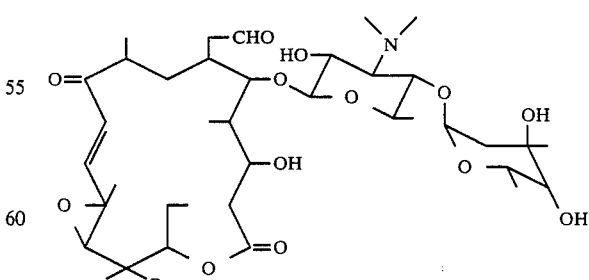

wherein R is OH.

* * * * *